United States Patent
Lai et al.

(10) Patent No.: US 7,423,074 B2
(45) Date of Patent: Sep. 9, 2008

(54) POLYSILOXANE PREPOLYMERS FOR BIOMEDICAL DEVICES

(75) Inventors: Yu-Chin Lai, Pittsford, NY (US);
Weihong Lang, Penfield, NY (US);
Edmond T. Quinn, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 257 days.

(21) Appl. No.: 11/292,817

(22) Filed: Dec. 2, 2005

(65) Prior Publication Data
US 2006/0142524 A1 Jun. 29, 2006

Related U.S. Application Data

(60) Provisional application No. 60/640,154, filed on Dec. 29, 2004.

(51) Int. Cl.
*G02B 1/04* (2006.01)
*C08F 290/06* (2006.01)

(52) U.S. Cl. .......... 523/106; 526/258; 526/264; 526/303.1; 526/310; 526/321; 526/328; 526/279; 528/25; 528/28; 528/44; 528/85; 523/107

(58) Field of Classification Search .......... None
See application file for complete search history.

(56) References Cited

U.S. PATENT DOCUMENTS

| | | | |
|---|---|---|---|
| 3,408,429 A | 10/1968 | Wichterle | |
| 3,660,545 A | 5/1972 | Wichterle | |
| 4,113,224 A | 9/1978 | Clark et al. | |
| 4,136,250 A | 1/1979 | Mueller et al. | |
| 4,197,266 A | 4/1980 | Clark et al. | |
| 4,605,712 A | 8/1986 | Mueller et al. | |
| 5,034,461 A | 7/1991 | Lai et al. | |
| 5,070,169 A * | 12/1991 | Robertson et al. | 528/25 |
| 5,260,000 A | 11/1993 | Nandu et al. | |
| 5,271,875 A | 12/1993 | Appleton et al. | |
| 5,449,729 A | 9/1995 | Lai | |
| 5,760,100 A | 6/1998 | Nicolson et al. | |
| 6,312,706 B1 | 11/2001 | Lai et al. | |
| 6,359,024 B2 * | 3/2002 | Lai | 522/64 |
| 6,545,114 B1 * | 4/2003 | Yang et al. | 528/26 |
| 6,750,309 B1 * | 6/2004 | Chu et al. | 528/28 |
| 6,815,074 B2 * | 11/2004 | Aguado et al. | 428/447 |
| 2003/0208016 A1 * | 11/2003 | Dershem et al. | 526/262 |
| 2006/0276605 A1 * | 12/2006 | Lai et al. | 526/279 |
| 2006/0276608 A1 * | 12/2006 | Lang et al. | 528/25 |

OTHER PUBLICATIONS

Yu-Chin Lai, "The Role of Bulky Polysiloxanylalkyl Methacrylates in Polyurethane-Polysiloxane Hydrogels", Journal of Applied Polymer Science, vol. 60, 1193-1199 (1996), John Wiley & Sons, Inc.

Yu-Chin Lai, "Novel Polyurethane-Silicone Hydrogels", Journal of Applied Polymer Science, vol. 56, 301-310 (1995), John Wiley & Sons, Inc.

* cited by examiner

*Primary Examiner*—Marc S Zimmer
(74) *Attorney, Agent, or Firm*—Joseph Barrera

(57) ABSTRACT

A polysiloxane copolymer that is useful for forming biomedical devices comprises blocks (I) and (II) and is terminated at each end with an ethylenically unsaturated radical:

$$(*Dii*Diol*Dii*PS)_x \qquad (I)$$

$$(*Dii*PS)_y \qquad (II)$$

wherein:
each Dii is independently a diradical residue of a diisocyanate;
each Diol is independently a diradical residue of a diol having 1 to 10 carbon atoms;
each PS is independently a diradical residue of a polysiloxane-containing diol or diamine;
each * is independently —NH—CO—NH—, —NH—COO— or —OCO—NH—:
x represents the number of blocks (I) and is at least 2, and y represents the number of blocks (II) and is at least 1.

24 Claims, No Drawings

POLYSILOXANE PREPOLYMERS FOR BIOMEDICAL DEVICES

This application claims priority under 35 USC 119(e) or prior provisional application Ser. No. 60/640,154, filed Dec. 29, 2004.

FIELD OF THE INVENTION

The present invention relates to polysiloxane prepolymers that are useful for forming biomedical devices, particularly ophthalmic devices including contact lenses, intraocular lenses and ophthalmic implants. This invention also relates to copolymers formed from the prepolymers, especially hydrogel copolymers.

BACKGROUND OF THE INVENTION

Hydrogels represent a desirable class of materials for the manufacture of various biomedical devices, including ophthalmic devices such as contact lenses. A hydrogel is a hydrated cross-linked polymeric system that contains water in an equilibrium state. Hydrogel lenses offer desirable biocompatibility and comfort. Silicone hydrogels are a known class of hydrogels and are characterized by the inclusion of a silicone-containing material. Typically, a silicone-containing monomer is copolymerized by free radical polymerization with a hydrophilic monomer, with either the silicone-containing monomer or the hydrophilic monomer functioning as a crosslinking agent (a crosslinker being defined as a monomer having multiple polymerizable functionalities) or a separate crosslinker may be employed. An advantage of silicone hydrogels over non-silicone hydrogels is that the silicone hydrogels typically have higher oxygen permeability due to the inclusion of the silicone-containing monomer.

Various polysiloxane-based prepolymers with urea or urethane linkages have been disclosed as potential silicone-containing monomers for silicone hydrogels. These various prepolymers may differ in their methods of preparation and in their physical characteristics/properties, and thus may exhibit divergent behavior when combined with other monomers for hydrogel copolymers.

One class of urethane- or urea-containing polysiloxane prepolymers involves polysiloxane-diol or polysiloxane-diamine endcapped with an ethylenically unsaturated monomer having an isocyanate group, such as isocyanatoethyl methacrylate (IEM). For example, by reacting IEM with hydroxy-terminated polydimethylsiloxane, a prepolymer is formed. In general, this class of prepolymer exhibits similar compatibility with hydrophilic monomers as corresponding prepolymers without the urethane linkage, especially for higher molecular weight prepolymers. Also, in general, these prepolymers are liquid at room temperature. Examples of such prepolymers are found in U.S. Pat. No. 4,605,712 (Mueller et al.).

A second class of urethane-containing polysiloxane prepolymers employs a diisocyanate to create urethane linkages. In general, these prepolymers are prepared by reacting 2 moles of diisocyanate with a hydroxy-terminated polydimethylsiloxane, followed by end capping with 2-hydroxyethyl methacrylate (HEMA). This class exhibits slight improvement in compatibility with hydrophilic monomers such as N,N-dimethylacrylamide (DMA), depending on the molecular weight of polysiloxane. Also, in general, this class of prepolymers is liquid at room temperature. Examples of such prepolymers are found in U.S. Pat. No. 4,136,250 (Mueller et al.)

U.S. Pat. No. 5,034,461 (Lai et al.) discloses various polysiloxane-containing urethane or urea prepolymers. Generally, these prepolymers are derived from a short chain diol, a hydroxy-terminated polydimethylsiloxane and a diisocyanate, such that the structures resemble a segmented polyurethane elastomer; these prepolymers are endcapped with polymerizable ethylenically unsaturated radicals, such as HEMA reacted with isocyanate. These prepolymers may be copolymerized with a hydrophilic comonomer to form a silicone hydrogel copolymer that is useful as a contact lens material or other biomedical device applications. The preferred prepolymers of U.S. Pat. No. 5,034,461 are composed of soft polysiloxane segments (represented by A in the patent formulae) and strong hard segments (represented by *D*G*D* in the patent formulae), and are endcapped with polymerizable ethylenically unsaturated radicals.

The polysiloxane-containing prepolymers of this invention comprise soft and strong hard segments as in U.S. Pat. No. 5,034,461. However, the prepolymers of this invention further comprise relatively weaker hard segments, in addition to the soft and strong hard segments. It has been found that this leads to several advantages. First, the present prepolymers tend to have a lower viscosity at room temperature, making them easier to process during synthesis and in casting biomedical devices as compared to prepolymers disclosed in U.S. Pat. No. 5,034,461. Second, this arrangement permits forming a prepolymer of higher silicone content, thereby permitting the formation of copolymers with higher oxygen permeabilities while maintaining good compatibility with hydrophilic monomer and forming clear hydrogels, as compared to prepolymers disclosed in U.S. Pat. Nos. 4,136,250 and 4,605,712. Third, because of the arrangements of the various segments, copolymers offering the higher oxygen permeabilities can be obtained without high modulus.

SUMMARY OF THE INVENTION

This invention provides a polysiloxane prepolymer that is useful for forming biomedical devices. The prepolymer comprises blocks (I) and (II) and is terminated at each end with an ethylenically unsaturated radical:

(*Dii*Diol*Dii*PS)$_x$     (I)

(*Dii*PS)$_y$     (II)

wherein:

each Dii is independently a diradical residue of a diisocyanate;

each Diol is independently a diradical residue of a diol having 1 to 10 carbon atoms;

each PS is independently a diradical residue of a polysiloxane-diol or -diamine;

each * is independently —NH—CO—NH—, —NH—COO— or —OCO—NH—:

x represents the number of blocks (I) and is at least 2, and y represents the number of blocks (II) and is at least 1.

Preferred prepolymers are represented by the general formulae:

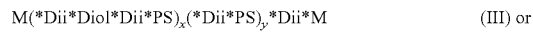

M(*Dii*Diol*Dii*PS)$_x$(*Dii*PS)$_y$*Dii*M     (III) or

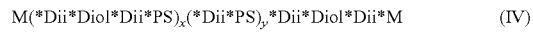

M(*Dii*Diol*Dii*PS)$_x$(*Dii*PS)$_y$*Dii*Diol*Dii*M     (IV)

wherein Dii, Diol, PS, *, x and y are as defined above, and M is independently a polymerizable ethylenically unsaturated radical.

This invention further provides a copolymer that is the polymerization product of a monomeric mixture comprising the prepolymer and a comonomer. One preferred comonomer is a hydrophilic monomer, and another preferred comonomer is a monofunctional silicone-containing monomer. Preferred copolymers are hydrogels that are the hydrated polymerization product of a monomeric mixture comprising the prepolymer and a hydrophilic comonomer. Especially preferred are hydrogel copolymers having a water content of at least 20 weight percent, a modulus no greater than 100 g/mm2, and/or an oxygen permeability of at least 100 barrers.

This invention further provides a biomedical device comprised of the copolymer, especially an ophthalmic device such as a contact lens or an intraocular lens.

DETAILED DESCRIPTION OF PREFERRED EMBODIMENTS

The prepolymers of this invention comprise blocks of formulae (I) and (II), represented above. Generally, the blocks of formula (I) may be characterized as composed of strong hard segments (represented by *Dii*Diol*Dii*) and soft segments (represented by PS). Generally, the blocks of formula (II) may be characterized as composed of weaker hard segments (represented by *Dii*) and soft segments (represented by PS). The distribution of these weaker and strong hard blocks (I) and (II) may be random or alternate, where x and y represent the total number of blocks of respective structures in the prepolymer; stated differently, it is not necessary in formulae (III) and (IV) that all blocks of formula (I) are directly linked to each other. The distribution of these blocks may be controlled by the sequence of addition of the polysiloxane, diisocyanate and short chain diol ingredients during the preparation of the prepolymer.

The prepolymers include polysiloxane-containing soft segments, represented by in formulae (I), (II), (III) and (IV). More particularly, this polysiloxane-containing segment is derived from polysiloxanes endcapped with hydroxyl or amino radicals:

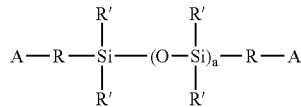

wherein each A is a hydroxyl or amino radical;

each R is independently selected from an alkylene group having 1 to 10 carbon atoms wherein the carbon atoms may include ether, urethane or ureido linkages therebetween;

each R' is independently selected from hydrogen, monovalent hydrocarbon radicals or halogen substituted monovalent hydrocarbon radicals wherein the hydrocarbon radicals have 1 to 20 carbon atoms which may include ether linkages therebetween, and a is at least 1.

Preferred R radicals are alkylene optionally substituted with ether radicals. Preferred R' radicals include: alkyl groups, phenyl groups, fluoro-substituted alkyl groups and alkenyl groups, optionally substituted ether groups. Especially preferred R' radicals include: alkyl, such as methyl; or fluoroalkyl optionally including ether linkages, such as —CH2-CH2-CH2-O—CH2-(CF2)z-H where z is 1 to 6.

Preferably, a is about 10 to about 100, more preferably about 15 to about 80. The Mn of PS ranges from 1000 to 8000, more preferably 2000 to 6000.

Various polysiloxane-diols and polysiloxane-diamines are commercially available. Additionally, representative syntheses of polysiloxanes are provided in the Examples.

The strong hard segments of the prepolymers include the residue of a diol, represented by Diol in formulae (I), (III) and (IV). Preferred Diol radicals include the diradical residue of an alkyl diol, a cycloalkyl diol, an alkyl cycloalkyl diol, an aryl diol or an alkylaryl diol having 1 to 10 carbon atoms and which may contain ether, thio or amine linkages in the main chain. Representative diols include 2,2-(4,4'-dihydroxydiphenyl)propane (bisphenol-A), 4,4'-iso-propylidine dicyclohexanol, ethoxylated and propoxylated bisphenol-A, 2,2-(4,4'-dihydroxydiphenyl)pentane, 1,1'-(4,4'-dihydroxydiphenyl)-p-diisopropyl benzene, 1,3-cyclohexane diol, 1,4 -cyclohexane diol, 1-4-cyclohexane dimethanol, neopentyl glycol, 1,4-butanediol, 1,3 -propanediol, 1,5-pentanediol, ethylene glycol, diethylene glycol and triethylene glycol. Especially preferred are alkylene and etherified alkylene diols having 1 to 10 carbon atoms.

The aforementioned polysiloxane-containing segments and diol residue segments are linked via diisocyanates that react with hydroxyl- or amino-functionality of the polysiloxane-containing segments and diols. Generally, any diisocyanate may be employed. These diisocyanates may be aliphatic or aromatic, and include alkyl, alkyl cycloalkyl, cycloalkyl, alkyl aromatic and aromatic diisocyanates preferably having 6 to 30 carbon atoms in the aliphatic or aromatic moiety. Specific examples include isophorone diisocyanate, hexamethylene-1,6-diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyanto methyl) cyclohexane, and cyclohexane diisocyanate.

Generally, higher x values results in prepolymers have a higher number of polar urethane/urea linkages, and polarity of the prepolymer is important to ensure compatibility with hydrophilic co-monomers. Generally, higher y values results in prepolymers with a higher percentage of silicon, resulting in higher oxygen permeability. However, the ratio of x and y should be balanced. Accordingly, the ratio of x to y is preferably at least 0.6 (i.e., x:y is at least 0.6:1), more preferably at least 0.75.

The prepolymers are endcapped at both ends with a polymerizable ethylenically unsaturated radical, represented by M in formulae (III) and (IV). Representative M radicals may be represented by the formula:

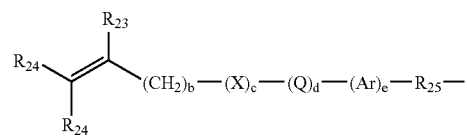

wherein:

$R_{23}$ is hydrogen or methyl;

each $R_{24}$ is hydrogen, an alkyl radical having 1 to 6 carbon atoms, or a —CO—Y—$R_{26}$ radical wherein Y is —O—, —S— or —NH—;

$R_{25}$ is a divalent alkylene radical having 1 to 10 carbon atoms;

$R_{26}$ is an alkyl radical having 1 to 12 carbon atoms;

Q denotes —CO—, —OCO— or —COO—;

X denotes —O— or —NH—;

Ar denotes an aromatic radical having 6 to 30 carbon atoms; b is 0 to 6; c is 0 or 1; d is 0 or 1; and e is 0 or 1.

Suitable endcapping precursors, for forming the M radicals, include: hydroxy-terminated (meth)acrylates, such as 2-hydroxyethylmethacrylate, 2-hydroxyethylacrylate, and 3-hydroxypropylmethacrylate; and amino-terminated (meth) acrylates, such as t-butylaminoethylmethacrylate and aminoethylmethacrylate; and (meth)acrylic acid. (As used herein, the term "(meth)" denotes an optional methyl substituent. Thus, terms such as "(meth)acrylate" denotes either methacrylate or acrylate, and "(meth)acrylic acid" denotes either methacrylic acid or acrylic acid.)

A first representative reaction scheme for forming the prepolymers is as follows. First, a diisocyanate is reacted with a diol, at a molar ratio of 2:1, respectively.

$$2x\text{OCN-Dii-NCO} + x\text{HO-Diol-OH} \rightarrow x\text{OCN-Dii*Diol*Dii-NCO}$$

In this scheme, * designates a urethane radical —NH—COO— or —OCO—NH—NH—: Generally, this reaction is conducted in the presence of a catalyst, such as dibutyl tin dilaurate and in a solvent, such as methylene chloride, and under reflux. Then, a diisocyanate and the polysiloxane-diol are added, with the ratio of total diisocyanates (x+y) to polysiloxane-diol being at least 1.1. (Generally, $2 < x+y \leq 11$; $x>0; y>0$.)

$$x \text{ OCN-(Dii-*-Diol-*-Dii-NCO} + (x+y-1)\text{HO—PS—OH} + y \text{ OCN-Dii-NCO} \rightarrow$$

$$\text{OCN-Dii*Diol*Dii*PS})_x(*\text{Dii*PS})_y*\text{Dii-NCO}$$

Finally, this product is endcapped with the polymerizable ethylenically unsaturated radical.

$$\text{OCN-(Dii*Diol*Dii*PS})_x(*\text{Dii*PS})_y*\text{Dii-NCO} + 2 \text{ M-OH} \rightarrow$$

$$\text{M(*Dii*Diol*Dii*PS})_x(*\text{Dii*PS})_y*\text{Dii*M}$$

A second representative reaction scheme for forming the prepolymers is as follows.

First, a diisocyanate is reacted with the polysiloxane-diol at a molar ratio shown below, where (1+1/m) preferably ranges from 1.05 to 1.9, most preferably from 1.2 to 1.5.

$$(m+1) \text{ OCN-Dii-NCO} + m \text{ HO-PS-OH} \rightarrow \text{OCN-(Dii*PS)}_m*\text{Dii-NCO}$$

In this scheme, * again designates a urethane radical —NH—COO—or —OCO—NH—. Generally, this reaction is conducted in the presence of a catalyst, such as dibutyl tin dilaurate and in a solvent, such as methylene chloride, and under reflux. Then, the diol is added, with the molar ratio selected based on the desired ratio of strong and weak hard segments, with reflux continued, where z1/z2 is equal to or lower than 2 but higher than 1.

$$z1 \text{ OCN-(Dii-*-PS)}_m*\text{-Dii-NCO} + z2 \text{ HO-Diol-OH} \rightarrow$$

$$\text{OCN-(Dii*Diol*Dii*PS)}_x(*\text{Dii*PS})_y*\text{Dii-NCO}$$

Finally, this product is endcapped with the polymerizable ethylenically unsaturated radical.

$$\text{OCN(Dii*Diol*Dii*PS)}_x(*\text{Dii*PS})_y*\text{Dii-NCO} + 2\text{M-OH} \rightarrow$$

$$\text{M(*Dii*Diol*Dii*PS)}_x(*\text{Dii*PS})_y*\text{Dii*M}$$

In the above reaction schemes, the reaction of diols with diisocyanates yields urethane radicals (—NH—COO— or —OCO—NH—). Alternatively, the reaction of diamines with diisocyantes would yield urea radicals (—NH—CO—NH—). Other methods for forming urethane or urea polymers are known in the art, and representative syntheses are illustrated in the Examples.

The copolymers of this invention are formed by copolymerizing the prepolymers of this invention with one or more comonomers. Since the prepolymers are endcapped with polymerizable ethylenically unsaturated radicals, they are polymerizable by free radical polymerization. The monomeric mixtures employed in the invention include conventional lens-forming or device-forming monomers. (As used herein, the term "monomer" or "monomeric" and like terms denote relatively low molecular weight compounds that are polymerizable by free radical polymerization, as well as higher molecular weight compounds also referred to as "prepolymers", "macromonomers", and related terms.) For copolymers, the subject prepolymers are included in the monomer mixture at 5 to 95 weight percent, preferably 20 to 70 weight percent.

A hydrophilic comonomer may be included in the initial monomeric mixture containing the subject prepolymer, for example, if it is desired to obtain a more hydrophilic copolymer or to form a hydrogel copolymer. Representative hydrophilic comonomers include: unsaturated carboxylic acids, such as methacrylic and acrylic acids; (meth)acrylic substituted alcohols, such as 2-hydroxyethylmethacrylate, 2-hydroxyethylacrylate and glyceryl methacrylate; vinyl lactams, such as N-vinyl pyrrolidone; and (meth)acrylamides, such as methacrylamide and N,N-dimethylacrylamide. A hydrogel is a crosslinked polymeric system that can absorb and retain water in an equilibrium state. For hydrogel copolymers, at least one hydrophilic monomer is included in the monomer mixture at 20 to 60 weight percent, preferably 25 to 50 weight percent.

Another class of lens-forming or device-forming monomers is silicone-containing monomers. In other words, another silicone-containing comonomer, in addition to the subject prepolymer, may be included in the initial monomeric mixture, for example, if it is desired to obtain a copolymer with higher oxygen permeability.

One suitable class of silicone containing monomers include known bulky, monofunctional polysiloxanylalkyl monomers represented by Formula (V):

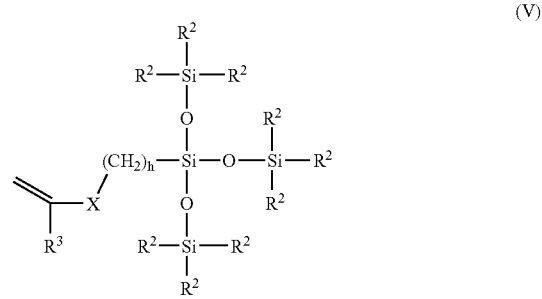

X denotes —COO—, —CONR$^4$—, —OCOO—, or —OCONR$^4$— where each where R$^4$ is H or lower alkyl; R$^3$ denotes hydrogen or methyl; h is 1 to 10; and each R$^2$ independently denotes a lower alkyl or halogenated alkyl radical, a phenyl radical or a radical of the formula —Si(R$^5$)$_3$ wherein each R$^5$ is independently a lower alkyl radical or a phenyl radical. Such bulky monomers specifically include methacryloxypropyl tris(trimethylsiloxy)silane (TRIS), pentamethyldisiloxanyl methylmethacrylate, tris(trimethylsiloxy) methacryloxy propylsilane, methyldi(trimethylsiloxy) methacryloxymethyl silane, 3-[tris(trimethylsiloxy)silyl] propyl vinyl carbamate, and 3-[tris(trimethylsiloxy)silyl] propyl vinyl carbonate.

Various difunctional and multifunctional silicone-containing monomers are known in the art and may be used as a comonomer if desired.

The monomer mixtures may include the silicone comonomer, in addition to the subject prepolymers, at 0 to 50 weight percent, preferably 5 to 30 weight percent when present.

In the case of silicone hydrogels, the monomer mixture includes a crosslinking monomer (a crosslinking monomer being defined as a monomer having multiple polymerizable functionalities). Since the subject prepolymers are endcapped at both ends with a polymerizable radical, the prepolymers will function as a crosslinker. Optionally, a supplemental crosslinking monomer may be added to the initial monomeric mixture. Representative crosslinking monomers include: divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and methacryloxyethyl vinylcarbonate. When a supplemental crosslinking agent is employed, this monomeric material may be included in the monomer mixture at 0.1 to 20 weight percent, more preferably at 0.2 to 10 weight percent.

In the case of intraocular lenses, the monomer mixtures may further include a monomer for increasing the refractive index of the resultant copolymer. Examples of such monomers are aromatic (meth) acrylates, such as phenyl (meth) acrylate, phenylethyl (meth)acrylate and benzyl (meth)acrylate.

An organic diluent may be included in the initial monomeric mixture. As used herein, the term "organic diluent" encompasses organic compounds that are substantially unreactive with the components in the initial mixture, and are often used to minimize incompatibility of the monomeric components in this mixture. Representative organic diluents include: monohydric alcohols, such as $C_2$-$C_{10}$ monohydric alcohols; diols such as ethylene glycol; polyols such as glycerin; ethers such as diethylene glycol monoethyl ether; ketones such as methyl ethyl ketone; esters such as methyl heptanoate; and hydrocarbons such as toluene.

In forming lenses or other biomedical devices, the monomeric mixtures may be charged to a mold, and then subjected to heat and/or light radiation, such as UV radiation, to effect curing, or free radical polymerization, of the monomer mixture in the mold. Various processes are known for curing a monomeric mixture in the production of contact lenses or other biomedical devices, including spincasting and static casting. Spincasting methods involve charging the monomer mixture to a mold, and spinning the mold in a controlled manner while exposing the monomer mixture to light. Static casting methods involve charging the monomer mixture between two mold sections forming a mold cavity providing a desired article shape, and curing the monomer mixture by exposure to heat and/or light. In the case of contact lenses, one mold section is shaped to form the anterior lens surface and the other mold section is shaped to form the posterior lens surface. If desired, curing of the monomeric mixture in the mold may be followed by a machining operation in order to provide a contact lens or article having a desired final configuration. Such methods are described in U.S. Pat. Nos. 3,408,429, 3,660,545, 4,113,224, 4,197,266, 5,271,875, and 5,260,000, the disclosures of which are incorporated herein by reference. Additionally, the monomer mixtures may be cast in the shape of rods or buttons, which are then lathe cut into a desired shape, for example, into a lens-shaped article.

One preferred application of the subject prepolymers is hydrogel contact lenses. For contact lens applications, it is preferred that the hydrogel copolymer, when fully hydrated, has a water content of at least 20 weight percent, as measured gravimetrically.

Also, it is preferred that the hydrogel copolymer has a tensile modulus no greater than 100 g/mm$^2$, more preferably a modulus between about 40 and 80 g/mm$^2$. Modulus may be measured with an Instron (Model 4502) instrument according to ASTM D-1708a, where the hydrogel copolymer film sample is immersed in borate buffered saline. An appropriate size of the film sample is gauge length 22 mm and width 4.75 mm, where the sample further has ends forming a dogbone shape to accommodate gripping of the sample with clamps of the Instron instrument, and thickness of 200±50 microns.

It is preferred that the hydrogel copolymer has an oxygen permeability of at least 100 barrers, more preferably, at least 150 barrers. Oxygen permeability (also referred to as Dk) is determined by the following procedure. The oxygen permeability of silicone hydrogels are measured by the polarographic method (ANSI Z80.20-1998) using an O2 Permeometer Model 201T instrument (Createch, Albany, Calif. USA) having a probe containing a central, circular gold cathode at its end and a silver anode insulated from the cathode. Measurements are taken only on pre-inspected pinhole-free, flat silicone hydrogel film samples of three different center thicknesses ranging from 150 to 600 microns. Center thickness measurements of the film samples may be measured using a Rehder ET-1 electronic thickness gauge. Generally, the film samples have the shape of a circular disk. Measurements are taken with the film sample and probe immersed in a bath containing circulating phosphate buffered saline (PBS) equilibrated at 35° C.+/−0.2°. Prior to immersing the probe and film sample in the PBS bath, the film sample is placed and centered on the cathode premoistened with the equilibrated PBS, ensuring no air bubbles or excess PBS exists between the cathode and the film sample, and the film sample is then secured to the probe with a mounting cap, with the cathode portion of the probe contacting only the film sample. For silicone hydrogel films, it is frequently useful to employ a Teflon polymer membrane, e.g., having a circular disk shape, between the probe cathode and the film sample. In such cases, the Teflon membrane is first placed on the pre-moistened cathode, and then the film sample is placed on the Teflon membrane, ensuring no air bubbles or excess PBS exists beneath the Teflon membrane or film sample. Once measurements are collected, only data with correlation coefficient value ($R^2$) of 0.97 or higher should be entered into the calculation of Dk value. At least two Dk measurements per thickness, and meeting $R^2$ value, are obtained. Using known regression analyses, oxygen permeability (Dk) is calculated from the film samples having at least three different thicknesses. Any film samples hydrated with solutions other than PBS are first soaked in purified water and allowed to equilibrate for at least 24 hours, and then soaked in PHB and allowed to equilibrate for at least 12 hours. The instruments are regularly cleaned and regularly calibrated using RGP standards. Upper and lower limits are established by calculating a ±8.8% of the Repository values established by William J. Benjamin, et al., *The Oxygen Permeability of Reference Materials*, Optom Vis Sci 7 (12s): 95 (1997), the disclosure of which is incorporated herein in its entirety:

| Material Name | Repository Values | Lower Limit | Upper Limit |
|---|---|---|---|
| Fluoroperm 30 | 26.2 | 24 | 29 |
| Menicon EX | 62.4 | 56 | 66 |
| Quantum II | 92.9 | 85 | 101 |

The following Examples illustrate various preferred embodiments of the invention.

EXAMPLE 1

Preparation of α,ω-bis(4-hydroxybutyl)polydimethylsiloxane (Mn about 5000)

The following were charged to a 2-L, three-neck round-bottom flask equipped with one reflux condenser: 51.26 grams of 1,3-bishydroxybutyl tetramethyldisiloxane; 1085 grams of dimethoxydimethylsilane; 157.8 grams of distilled water; and 18.4 mL of concentrated hydrochloric acid. The mixture was heated at 60° C. for 1 hour. Methanol was then distilled off over a 5-hour period, with 552 mL collected. Then, 349 ml distilled water and 349 mL concentrated HCl were added, and the contents were refluxed at 100° C. for 3 hours. The crude product was then separated from the aqueous layer. Then, 600 mL diethyl ether (ether) and 400 mL deionized water were added, and the solution was extracted twice with 400 mL sodium bicarbonate solution (0.5%) and then with distilled water until the washing had neutral pH. The product (655.8 grams) was then added slowly into a mixture of methanol/water (508.2 g/147.97 g). The bottom organic layer was separated, added with diethyl ether and dried with magnesium sulfate. Ether was then stripped under vacuum at room temperature and the residue was further stripped under vacuum (0.07-mm torr) at 80° C. The final product was recovered. The molecular weight (Mn) as determined by H-NMR was 4800.

EXAMPLE 2

Preparation of α,ω-bis(4-hydroxybutyl)polydimethylsiloxane (Mn about 2700)

The general procedure of Example 1 was following for making this polysiloxane, except the molar ratio of 1,3-bishydroxybutyl tetramethyldisiloxane to dimethoxydimethylsilane was changed to about 1:28. The molecular weight (Mn) of the product as determined by titration was 2730.

EXAMPLE 3

Preparation of a Polydimethylsiloxane-Based Prepolymer Using PDMS of Example 1

A dry 3-neck, 500-mL round-bottom flask was connected to a nitrogen inlet tube and a reflux condenser. The following were added to the flask all at once: isophorone diisocyanate (2.111 g, 9.497 mmol) (IPDI); diethyleneglycol (0.498 g, 4.696 mmol) (DEG); dibutyl tin dilaurate (0.161 g); and 150 mL methylene chloride. The contents were refluxed. After overnight, the amount of isocyanate decreased to 43.3% as determined by titration. Then α,ω-bis(4-hydroxybutyl)polydimethylsiloxane (45.873 g, 9.557 mmol) from Example 1 was added to the flask. The refluxing was continued overnight, and no unreacted isocyanate remained as determined by titration. Then, IPDI (1.261 g, 5.673 mmol) was added and the reflux was continued overnight. The amount of isocyanate decreased to 22.9% as determined by titration. The contents were cooled down to ambient temperature. 1,1'-bi-2-naphthol (0.008 g) and 2-hydroxyethyl methacrylate (0.429 g, 3.296 mmol) were then added and the contents were stirred at ambient until isocyanate peak at 2267 cm$^{-1}$ disappeared from IR spectrum of the product (about 20 hours). The solvent was then stripped under reduced pressure and the 44.55 g of product was recovered. Theoretically, the prepolymer had 3 strong hard segments, 4 weak hard segments (x about 3, y about 4).

EXAMPLE 4

Preparation of a Polydimethylsiloxane-Based Prepolymer Using PDMS of Example 1

A dry 3-neck, 500-mL round-bottom flask was connected to a nitrogen inlet tube and a reflux condenser. The following were added to the flask all at once: isophorone diisocyanate (7.825 g, 35.202 mmol) (IPDI); α,ω-bis(4-hydroxybutyl)polydimethylsiloxane (94.31 g, 19.648 mmol) from Example 1; dibutyl tin dilaurate (0.297 g); and 250 mL methylene chloride. The contents were refluxed. After overnight, the amount of isocyanate was determined to decrease to 44.5% by titration. Then diethyleneglycol (1.421 g, 13.391 mmol) (DEG) was added to the flask. The refluxing was continued for overnight, and the amount of isocyanate was dropped down to 5.1% of the original as determined by titration. Then the contents were cooled down to ambient temperature. 1,1'-bi-2-naphthol (0.013 g) and 2-hydroxyethyl methacrylate (0.819 g, 6.293 mmol) were then added and the contents were stirred at ambient until isocyanate peak at 2267 cm$^{-1}$ disappeared from IR spectrum of the product (about 20 hours). The solvent was then stripped under reduced pressure and the 82 g of product was recovered. Theoretically, the prepolymer had 4 strong hard segments, 3 weak hard segments (x about 4, y about 3).

EXAMPLE 5

Preparation of a Polydimethylsiloxane-Based Prepolymer Using PDMS of Example 1

A prepolymer with components of similar molar ratios as that of Example 4 was prepared. This synthesis was similar to Example 4 except a second batch of polysiloxane of about the same molecular weight was used. The amounts of components were: isophorone diisocyanate (8.716 g, 39.209 mmol); α,ω-bis(4-hydroxybutyl)-polydimethylsiloxane (105.23 g, 21.923 mmol); dibutyl tin dilaurate (0.307 g); 250 mL methylene chloride; diethyleneglycol (1.496 g, 14.093 mmol); 1,1'-bi-2-naphthol (0.0146 g); and 2-hydroxyethyl methacrylate (1.033 g, 7.938 mmol).

EXAMPLE 6

Preparation of a Polydimethylsiloxane-Based Prepolymer Using PDMS of Example 2

A dry 3-neck, 500 mL round-bottom flask was connected to a nitrogen inlet tube and a reflux condenser. The following were added to the flask all at once: IPDI (10.3311 g, 46.475 mmol); α,ω-bis(4-hydroxybutyl)polydimethylsiloxane (84.68 g, 31.023 mmol) from Example 2; dibutyl tin dilaurate (0.300 g); and 200 mL of methylene chloride. The contents were refluxed. After overnight, the amount of isocyanate was determined to decrease to 33.6% by titration. Then, DEG (1.092 g, 10.288 mmol) was added to the flask. The refluxing was continued for 60 hours, and the amount of isocyanate was dropped down to 11.4% of the original as determined by titration. Then, the contents were cooled down to ambient temperature. 1,1'-bi-2-naphthol (0.012 g) and 2-hydroxyethyl methacrylate (1.639 g, 12.595 mmol) were then added and the contents were stirred at ambient until isocyanate peak at 2267 cm$^{-1}$ disappeared from IR spectrum of the product (about 20 hours). The solvent was then stripped under reduced pressure to yield a clear liquid product (96.67 g). Theoretically the prepolymer has 6 PDMS block and 2 strong hard segments (x about 2, y about 5).

EXAMPLES 7-12

Copolymers from Prepolymer of Example 3

Monomer mixtures were made by mixing the following components, listed in Table 1 at amounts per weight: prepolymers of Examples 3 and 4; methacryloxypropyl tris(trimethylsiloxy)silane (TRIS); N,N-dimethylacrylamide (DMA); 2-hydroxy ethyl methacrylate (HEMA); N-vinyl pyrrolidone (NVP); and methacryloxyethyl vinylcarbonate (HemaVC). Additionally, each monomer mixture included: 1,4-bis(2-methacrylamidoethylamino)anthraquinone as a tint (150 ppm); hexanol as a diluent (10 parts by weight); and Darocur-1173™ UV initiator (Ciba Specialty Chemical, Ardsley N.Y.) (0.5 wt %).

The monomer mixtures were cast between silane-treated glass plates, and then cured under UV light for 1 hour. Each monomer mixture was cast between three sets of glass plates, each set of plates separated by Teflon™ polymer tapes of different thicknesses, such that three sets of film samples were obtained for each monomer mixture, with film thicknesses of about 200, 400 and 600 microns. The cured films were then extracted with isopropanol overnight, followed by hydration in deionized (DI) water, boiled in DI water for 4 hours and then saturated in borate buffered saline or phosphate buffered saline to give hydrogel films. The water content was measured gravimetrically. Mechanical tests were conducted in borate buffered saline according to ASTM D-1708a, discussed above. The oxygen permeabilities, reported in Dk (or barrer) units, were measured in phosphate buffered saline at 35° C., using acceptable films with three different thicknesses, as discussed above.

TABLE 1

| | Example | | | | | |
|---|---|---|---|---|---|---|
| | 7 | 8 | 9 | 10 | 11 | 12 |
| Prepolymer Ex 3 | 65 | 65 | 60 | 65 | 65 | 60 |
| Tris | 10 | 10 | 15 | 10 | 10 | 15 |
| DMA | 25 | 12 | 12 | 12 | 12.4 | 0 |
| NVP | — | 13 | 10 | 10 | 10 | 22 |
| Hema | — | 5 | 5 | 2.65 | 2.4 | 5 |
| HemaVC | — | 0.5 | 0.5 | 0.5 | 0.5 | 0.5 |
| % Water | 34.2 | ND | ND | 31.7 | 33.9 | 36.5 |
| Dk (barrer) | —$^{(1)}$ | ND | ND | 251 | 208 | 169$^{(2)}$ |
| Modulus (g/mm$^2$) | 45 | ND | ND | 57 | — | — |

The monomer mixtures prepared in Examples 8 and 9 were cloudy so no films were cast. However, when less HEMA was used as a hydrophilic comonomer (as in Examples 9, 10 and 11), or when DMA was replaced totally with NVP (as in Example 6), the mixes were clear and all hydrogel films were clear. (1) Three thickness data points were not obtained. (2) Four thickness data points were obtained.

EXAMPLES 13-18

Copolymers from Prepolymer of Example 4

Following the general procedures of Examples 7-12, monomer mixtures were prepared, copolymer films were cast, and properties were evaluated, using the prepolymer of Example 4. The results are summarized in Table 2.

TABLE 2

| | Example | | | | | |
|---|---|---|---|---|---|---|
| | 13 | 14 | 15 | 16 | 17 | 18 |
| Prepolymer Ex 4 | 65 | 65 | 60 | 65 | 60 | 65 |
| Tris | 10 | 10 | 15 | 10 | 15 | 10 |
| DMA | 25 | 12 | 12 | 12 | 0 | 0 |
| NVP | — | 10 | 10 | 10 | 22 | 22 |
| Hema | — | 0 | 5 | 5 | 5 | 5 |
| HemaVC | — | 0.5 | 0.5 | 0.5 | 0.5 | 0.5 |
| % Water | 31.7 | 28.5 | 29.6 | 34.7 | 48.2 | 47.8 |
| Dk (barrer) | 158 | 208 | 218 | 209 | 215 | 183 |
| Modulus (g/mm$^2$) | 60 | 66 | 54 | 61 | 73 | 76 |

When comparing the prepolymers of Example 3 and Example 4, it was found that the prepolymer of Example 4 can be used to formulate with 5 parts of HEMA, instead of only 2.5 parts as with the prepolymer of Example 3. It is believed this is because the prepolymer of Example 4 had more strong hard segment content than the prepolymer of Example 3.

EXAMPLES 19-24

Copolymers Derived from Prepolymer of Example 5

Following the general procedures of Examples 7-12, monomer mixtures were prepared, copolymer films were cast, and properties were evaluated, using the prepolymer of Example 5. The results are summarized in Table 3.

TABLE 3

| | Example | | | | | |
|---|---|---|---|---|---|---|
| | 19 | 20 | 21 | 22 | 23 | 24 |
| Prepolymer Ex 5 | 65 | 65 | 65 | 65 | 60 | 60 |
| Tris | 10 | 10 | 10 | 10 | 15 | 15 |
| DMA | 4 | 8 | 12 | 12 | 0 | 0 |
| NVP | 18 | 14 | 10 | 10 | 22 | 25 |
| Hema | 3 | 3 | 3 | 5 | 5 | 5 |
| HemaVC | 0.9 | 0.7 | 0.5 | 0.5 | 1.0 | 0.5 |
| % Water | 26.9 | 27.8 | 28.0 | 28.8 | 26.8 | 36.4 |
| Dk (barrer) | — | — | — | — | 287 | — |
| Modulus (g/mm$^2$) | 96 | 84 | 74 | 73 | 107 | 73 |

EXAMPLES 25-27

Copolymers Derived from Prepolymer of Example 6

Following the general procedures of Examples 7-12, monomer mixtures were prepared, copolymer films were cast, and properties were evaluated, using the prepolymer of Example 6. The results are summarized in Table 4.

TABLE 4

|  | Example | | |
| --- | --- | --- | --- |
|  | 25 | 26 | 27 |
| Prepolymer Ex 6 | 65 | 65 | 60 |
| Tris | 10 | 10 | 15 |
| DMA | 25 | 12 | 12 |
| NVP | — | 10 | 10 |
| Hema | — | 5 | 5 |
| HemaVC | — | 0.5 | 0.5 |
| % Water | 29.8 | 23.6 | 25.8 |
| Dk (barrer) | 122 | 165 | 161 |
| Modulus (g/mm$^2$) | 81 | 119 | 84 |

Having thus described various preferred embodiment of the invention, those skilled in the art will appreciate that various modifications, additions, and changes may be made thereto without departing from the spirit and scope of the invention, as set forth in the following claims.

We claim:

1. A copolymer that is the polymerization product of a monomeric mixture comprising a copolymer represented by the general formulae, M(*Dii*Diol*Dii*PS)$_x$(*Dii*PS)$_y$*Dii*M or M(*Dii*Diol*Dii*PS)$_x$(*Dii*PS)$_y$*Dii*Diol*Dii*M wherein:
each M is independently a polymerizable ethylenically unsaturated radical;
each Dii is independently a diradical residue of a diisocyanate;
each Diol is independently a diradical residue of a diol having 1 to 10 carbon atoms;
each PS is independently a diradical residue of a polysiloxane-diol or a polysiloxane diamine;
each * is independently —NH—CO—NH—, —NH—COO— or —OCO—NH—;
x is at least 2, and
y is at least 1; and
a hydrophilic comonomer and a monofunctional silicone-containing monomer.

2. The copolymer of claim 1, wherein each Dii is independently a diradical residue of an aliphatic or an aromatic diisocyanate having 6 to 30 carbon atoms in the aliphatic or aromatic moiety.

3. The copolymer of claim 2, wherein each Dii is a diradical residue of a diisocyanate selected from the group consisting of isophorone diisocyanate, hexamethylene-1,6-diisocyanate, 4,4'-dicyclohexylmethane diisocyanate, toluene diisocyanate, 4,4'-diphenyl diisocyanate, 4,4'-diphenylmethane diisocyanate, p-phenylene diisocyanate, 1,4-phenylene 4,4'-diphenyl diisocyanate, 1,3-bis-(4,4'-isocyanto methyl) cyclohexane, and cyclohexane diisocyanate.

4. The copolymer of claim 1, wherein each Diol is independently selected from the group consisting of an alkyl diol, a cycloalkyl diol, an alkyl cycloalkyl diol, an aryl diol or an alkylaryl diol having 1 to 10 carbon atoms and which may contain ether, thio or amine linkages in the main chain.

5. The copolymer of claim 4, wherein each Diol is independently selected from the group consisting of 2,2-(4,4'-dihydroxydiphenyl)propane (bisphenol-A), 4,4'-iso-propylidine dicyclohexanol, ethoxylated and propoxylated bisphenol-A, 2,2-(4,4'-dihydroxydiphenyl)pentane, 1,1'-(4,4'-dihydroxydiphenyl)-p-diisopropyl benzene, 1,3-cyclohexane diol, 1,4-cyclohexane diol, 1-4-cyclohexane dimethanol, neopentyl glycol, 1,4-butanediol, 1,3-propanediol, 1,5-pentanediol, ethylene glycol, diethylene glycol and triethylene glycol.

6. The copolymer of claim 1, wherein each PS is independently a diradical residue of a polysiloxane represented by the formula:

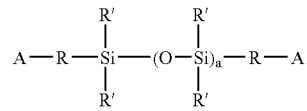

wherein:
each A is a hydroxyl or an amino radical;
each R is independently selected from an alkylene group having 1 to 10 carbon atoms wherein the carbon atoms may include ether, urethane or ureido linkages therebetween;
each R' is independently selected from hydrogen, monovalent hydrocarbon radicals or halogen substituted monovalent hydrocarbon radicals wherein the hydrocarbon radicals have 1 to 20 carbon atoms which may include ether linkages therebetween, and
a is at least 1.

7. The copolymer of claim 6, wherein each R is alkylene, and each R' is independently alkyl or fluoroalkyl optionally including ether linkages.

8. The copolymer of claim 6, wherein Mn of PS ranges from 1000 to 8000.

9. The copolymer of claim 1, wherein the ratio of x to y is at least 0.6.

10. The copolymer of claim 1, wherein each M is independently a polymerizable ethylenically unsaturated radical of the formula:

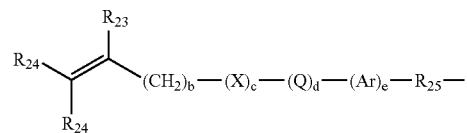

wherein:
R$^{23}$ is hydrogen or methyl;
each R$^{24}$ is hydrogen, an alkyl radical having 1 to 6 carbon atoms, or a —CO—Y—R$_{26}$ radical wherein Y is —O—, —S— or —NH—;
R$^{25}$ is a divalent alkylene radical having 1 to 10 carbon atoms;
R$^{26}$ is a alkyl radical having 1 to 12 carbon atoms;
Q is —CO—, —OCO— or —COO—;
X is —O— or —NH—;
Ar is an aromatic radical having 6 to 30 carbon atoms;
b is 0 to 6; c is 0 or 1; d is 0 or 1; and e is 0 or 1.

11. The copolymer of claim 1, wherein:
each M is methacryloxyethyl;
each Dii is the diradical residue of isophorone diisocyanate;
each Diol is the diradical residue of diethyleneglycol;
each PS is a diradical residue of a polydimethylsiloxane-diol having Mn of at least 2000; and
each * is —NH—COO— or —OCO—NH—.

12. The copolymer of claim 1, wherein the hydrophilic monomer selected form the group consisting of: ethylenically unsaturated carboxylic acids; (meth)acrylic substituted alcohols; vinyl lactams; and (meth)acrylamides.

13. The copolymer of claim 12, wherein the hydrophilic monomer selected form the group consisting of: methacrylic acid; acrylic acid; 2-hydroxyethylmethacrylate; glyceryl methacrylate; N-vinyl pyrrolidone; methacrylamide; and N,N-dimethylacrylamide.

14. The copolymer of claim 1, wherein the monofunctional silicone-containing monomer is methacryloxypropyl tris(trimethylsiloxy)silane.

15. A hydrogel copolymer that is the hydrated polymerization product of a monomeric mixture comprising a copolymer represented by the general formulae, $$M(*Dii*Diol*Dii*PS)_x(*Dii*PS)_y*Dii*M \text{ or}$$

$$M(*Dii*Diol*Dii*PS)_x(*Dii*PS)_y*Dii*Diol*Dii*M$$

wherein;
- each M is independently a polymerizable ethylenically unsaturated radical;
- each Dii is independently a diradical residue of a diisocyanate;
- each Diol is independently a diradical residue of a diol having 1 to 10 carbon atoms;
- each PS is independently a diradical residue of a polysiloxane-diol or a polysiloxane diamine;
- each * is independently —NH—CO—NH—, —NH—COO— or —OCO—NH—;
- x is at least 2, and
- y is at least 1; and
- a hydrophilic comonomer and a monofunctional silicone-containing monomer.

16. The hydrogel copolymer of claim 15, having a water content of at least 20 weight percent.

17. The hydrogel copolymer of claim 15, having a modulus no greater than 100 g/mm$^2$.

18. The hydrogel copolymer of claim 17, having a modulus between about 40 and 80 g/mm$^2$.

19. The hydrogel copolymer of claim 15, having an oxygen permeability of at least 100 barrers.

20. The hydrogel copolymer of claim 19, having an oxygen permeability of at least 150 barrers.

21. The hydrogel copolymer of claim 15, having a water content of at least 20 weight percent, a modulus between about 40 and 80 g/mm$^2$, and an oxygen permeability of at least 150 barrers.

22. A biomedical device comprising a copolymer of claim 15.

23. An ophthalmic device comprising a copolymer of claim 15.

24. The ophthalmic device of claim 23, that is a contact lens or an intraocular lens.

* * * * *